(12) United States Patent
Mekid et al.

(10) Patent No.: US 8,442,777 B1
(45) Date of Patent: May 14, 2013

(54) SYSTEM AND METHOD FOR MEASURING ROLLING RESISTANCE

(71) Applicant: King Fahd University of Petroleum and Minerals, Dhahran (SA)

(72) Inventors: Samir Mekid, Dhahran (SA); Igor Gilavdary, Minsk (BY); Natalia Riznookaya, Zhlobin (BY)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 13/652,433

(22) Filed: Oct. 15, 2012

(51) Int. Cl.
*G01B 3/00* (2006.01)
*G01N 3/56* (2006.01)

(52) U.S. Cl.
USPC .................................. 702/33; 73/9

(58) Field of Classification Search .............. 702/33, 702/40, 41, 89; 73/9
See application file for complete search history.

(56) References Cited

U.S. PATENT DOCUMENTS

| | | | | |
|---|---|---|---|---|
| 2,058,784 | A * | 10/1936 | Hoff et al. ..................... | 73/480 |
| 3,161,704 | A * | 12/1964 | Le Grand et al. ............. | 264/40.1 |
| 3,400,571 | A * | 9/1968 | Cheetham ...................... | 73/9 |
| 3,643,490 | A | 2/1972 | Hertel | |
| 4,185,503 | A | 1/1980 | Saito | |
| 5,635,623 | A | 6/1997 | Simon | |
| 6,494,076 | B1 | 12/2002 | Gent et al. | |
| 7,249,520 | B1 | 7/2007 | Zhu et al. | |
| 7,483,808 | B2 * | 1/2009 | Greiner et al. ............. | 702/166 |
| 2007/0169539 | A1 * | 7/2007 | Fujii et al. ................. | 73/9 |
| 2007/0205879 | A1 * | 9/2007 | Matsuda et al. ............ | 340/438 |
| 2008/0115563 | A1 * | 5/2008 | Potts ............................ | 73/9 |

FOREIGN PATENT DOCUMENTS

GB 1 400 841 7/1975

* cited by examiner

*Primary Examiner* — Jonathan C Teixeira Moffat
*Assistant Examiner* — Timothy H Hwang
(74) *Attorney, Agent, or Firm* — Richard C. Litman

(57) ABSTRACT

The system and method for measuring rolling resistance provide for the measurement of various properties associated with pre-rolling resistance. A cruciform pendulum is formed from a rigid rod having opposed upper and lower ends and a horizontal support extending orthogonal thereto. A pair of substantially hemispherical samples formed from a first material are mounted on opposing ends of the horizontal support. Flat, planar samples of a second test material are placed upon spaced apart supporting surfaces. The cruciform pendulum is suspended between the supporting surfaces with the hemispherical first material resting on the planar second material. The rigid rod is deflected from vertical and released to induce pendulum oscillations with the first material rolling on the second material. Based upon the measured angular deviations and periods of pendulum oscillations, coefficients of rolling friction, moments of rolling friction, hysteresis losses, adhesion and moments of elastic rolling resistance may be easily calculated.

16 Claims, 2 Drawing Sheets

SYSTEM AND METHOD FOR MEASURING ROLLING RESISTANCE

BACKGROUND OF THE INVENTION

1. Field of the Invention

The present invention relates to testing and measurement devices, and particularly to a system and method for measuring rolling resistance during pre-rolling, and more particularly, to a system and method for measuring the moment of forces of resistance, dimensionless coefficients of rolling friction, and the hysteretic losses on both uncoated and coated surfaces.

2. Description of the Related Art

Rolling resistance, sometimes referred to as "rolling friction" or "rolling drag", is the resistance that occurs when a round object, such as a ball, tire, or wheel, rolls on a surface. The rolling resistance is primarily caused by the deformation of the object, the deformation of the surface, and movement below the surface. Additional contributing factors include wheel diameter, forward speed, the load on the wheel, surface adhesion, sliding, relative micro-sliding between the surfaces of contact, and their roughness. The rolling resistance greatly depends on the material of the wheel or tire and the type of ground or other surface. What might be termed "basic rolling resistance" is steady velocity and straight line motion on a level surface, but there also exists rolling resistance when accelerating, when on curves, and when on a grade.

Rolling resistance may be defined as the moment a rolling force) needed to overcome resistance to rotation and to move forward. The rolling resistance is much smaller than the sliding friction between two surfaces under equal loads, typically by a factor of at least one hundred. During the rolling process, it is possible for micro-slip to occur in a region within the contact area, inducing loss of mechanical energy through friction, thus leading to hysteresis loss and non-local memory, as is observed in pre-rolling. Rolling slowly from rest exhibits increasing rolling resistance, which starts from zero to steady-state rolling with constant rolling resistance. In this range of pre-rolling, the rolling resistance has a non-linear behavior. The pre-rolling stage induces hysteresis, which is typically difficult to measure due to its non-linearity.

In rolling friction, two separate stages must be considered. The first stage is the pre-rolling stage, in which the deformation forces are dominant and the patch contact includes sub-regions of adhesion and slip. The second stage is the steady rolling stage in which the rolling resistance has been fully developed to its maximum value and has more pronounced rotation.

The linear and large-scale steady rolling stage is relatively easy to describe and measure. The pre-rolling stage, however, not only includes non-linear considerations, but occurs only on a very small scale of pre-movement. Thus, it would be desirable to be able to easily make measurements of rolling resistance during the pre-rolling stage.

Thus, a system and method for measuring rolling resistance solving the aforementioned problems is desired.

SUMMARY OF THE INVENTION

The system and method for measuring rolling resistance provide for the measurement of various properties associated with pre-rolling resistance. A cruciform pendulum is formed from a rigid rod having opposed upper and lower ends, and a horizontal support mounted on a central portion of the rigid rod. The upper and lower ends of the rod are both free to rotate. The horizontal support extends along an axis orthogonal to the axis of the rigid rod, forming the cruciform shape. A pair of retainers are respectively secured to horizontally-opposed ends of the horizontal support and extend downward therefrom. The retainers hold a pair of substantially hemispherical samples (or spherical or ball-shaped samples having a hemispherical portion extending below the retainer) formed from a first material. The hemispherical samples bear upon, and are balanced on, a corresponding pair of flat surface samples formed from a second material. The weight of the cruciform pendulum is supported by the hemispherical samples depending from opposite ends of the horizontal support, and the instantaneous axis of rotation of the pendulum is through the points where the hemispherical (or ball-shaped) samples bear upon the flat surface samples.

An angular deviation $\phi$ of the axis of the rigid rod with respect to the vertical is optically measured. Preferably, the pendulum achieves an angular deviation $\phi$ in the range $$\phi \leq 0.1 \frac{a}{R},$$

where a is a radius of a contact spot between each hemispherical sample and the corresponding one of the flat surface samples, and R is a radius of each hemispherical sample, A current time t and a period of oscillation $T_i$ for each cycle of oscillation of the pendulum are then measured by a timer. Each period $T_i$ corresponds to a time $t_i$, where i is an integer ranging between zero and n, where n represents a final measurement.

It is useful to calculate amplitudes of oscillation $\alpha_i$ as $$\alpha_i = \phi(t_i)\sec\left(\frac{2\pi}{T}t_i\right),$$

where T is a mean value of the set $T_i$, and where an initial amplitude is given as $\alpha_\phi$ and a final amplitude of oscillation is given as $\alpha_n$. From this, a dimensionless coefficient of rolling friction f between the pair of hemispherical samples and stationary flat surface samples, formed from a second material, may be calculated as $$f = \frac{\cos\alpha_n - \cos\alpha_0}{2(\alpha_0 + \alpha_n) + 4\sum_{i=1}^{n-1}\alpha_i}.$$

In addition to the calculation of the dimensionless coefficient of rolling friction, which is time-independent, an instantaneous coefficient of rolling friction, as well as a moment of rolling friction, may be calculated as a function of the angular deflection $\phi$ and an instantaneous moment of rolling friction. Further, hysteresis losses for each cycle of the pendulum oscillation, the pressure of adhesion attraction between the pair of hemispherical samples and stationary flat surface samples, and the moment of elastic rolling resistance may also be calculated.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
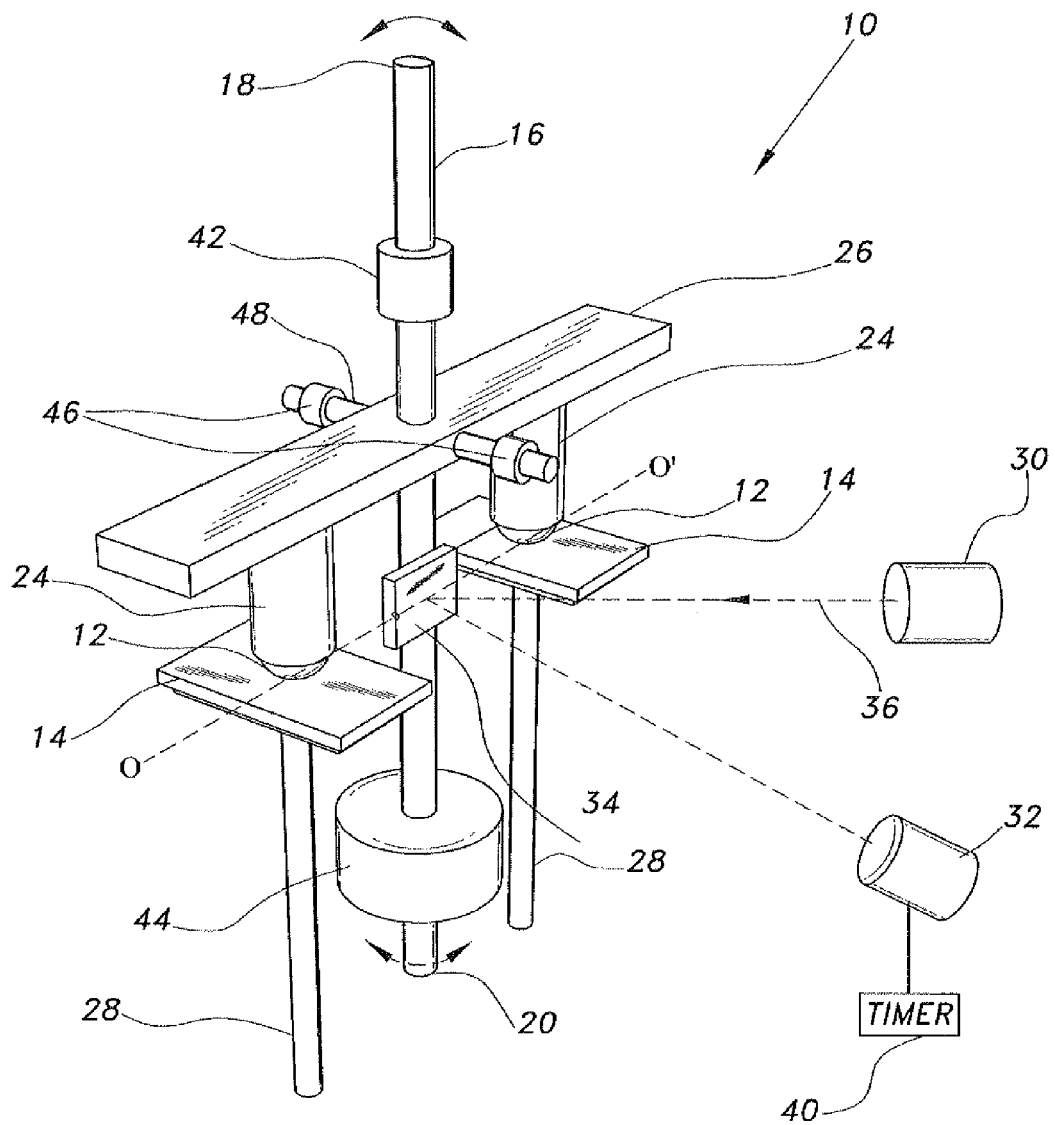
FIG. 1 is a perspective view of a system for measuring rolling resistance according to the present invention.

As shown in FIG. 1, the system for measuring rolling resistance, designated generally as 10, is based on pendulum motion for measuring rolling resistance parameters between hemispherical samples 12, formed from a first material, and flat surface samples 14, which are formed from a second material. It should be understood that both first and second material samples may be varied, thus allowing the system 10 to be used for measurement of rolling resistance between any two desired materials. Additionally, since the point of contact is where the frictional effects take place, it should be understood that the hemispherical samples 12 may be coated with the material of interest, rather than being wholly formed from the material.

The system 10 includes a rigid rod 16 having an upper end 18 and a lower end 20. Both upper end 18 and lower end 20 are free to rotate in oscillatory fashion. In the particular exemplary configuration of FIG. 1, the rod 16 oscillates back and forth in the left-right direction (i.e., in the plane of the page). Motion during the pre-rolling stage is of primary importance. Thus, it should be understood that the pendulum motion of the rigid rod 16 is very small.

As shown in FIG. 1, a horizontal support 26 is mounted to a central portion of rigid rod 16, forming a cruciform pendulum. A pair of holders 24 extend downward from opposite ends of the horizontal support 26. The pair of hemispherical samples 12 (or ball-shaped samples having a hemispherical portion protruding from the holders 24) are mounted to the respective lower ends of holders 24. The samples 12 are hemispherical to provide accurate simulation of spherical balls experiencing rolling. It is important to note that the hemispherical samples 12 are fixed with respect to the holders 24; i.e., they do not rotate in holders 24, but with the holders 24. This is because only pre-rolling considerations are being taken into account. Thus, additional rolling of the samples 12 is not being measured. The samples 12 contact and bear upon the flat surface samples 14, which are supported by stands 28, which remain fixed with respect to the pendulum motion. The entire system 10 is balanced on samples 14 at the contacting spots of the hemispherical samples 12. Thus, the system 10 is a cruciform pendulum balanced on these spots, and the instantaneous axis of rotation of the entire pendulum is through an axis O-O' extending through a tangent to the hemispherical samples 12 extending through the spots that the hemispherical samples 12 bear upon. The center of mass of the cruciform pendulum is located centrally between upper ends of the hemispherical portions.

Figure 2:
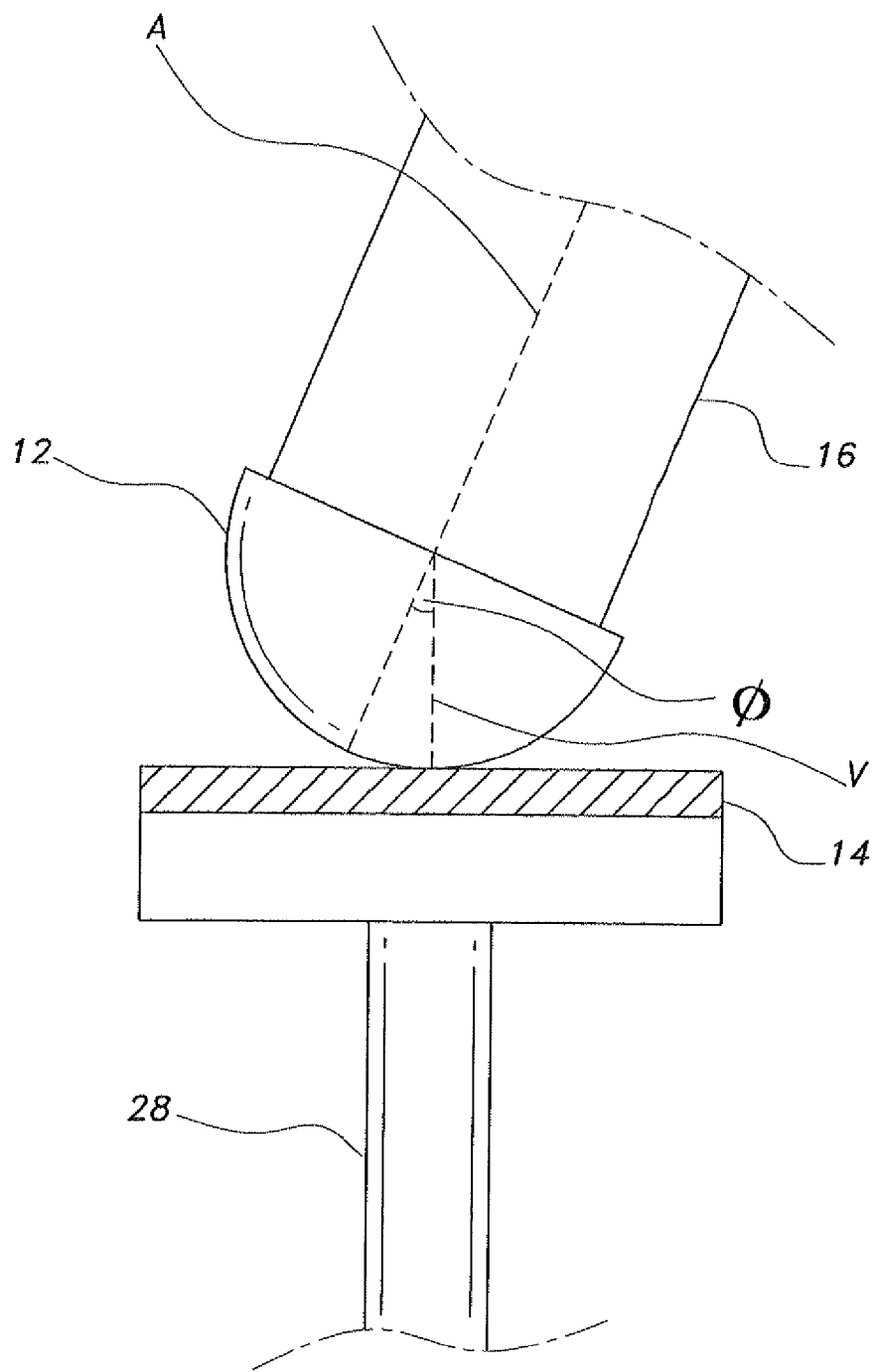
FIG. 2 is a partial side view of the system for measuring rolling resistance of FIG. 1, diagrammatically illustrating rolling contact between a hemispherical sample and a flat test substrate.

As shown in FIG. 2, as the rigid rod 16 rotates very slightly, the hemispherical sample 12 enters the pre-rolling stage, tipping slightly such that its axis (corresponding to the axis A of rigid rod 16) is angled with respect to the vertical V by an angle $\phi$. The angle $\phi$ is also the angular position of the oscillation of rigid rod 16 with respect to the vertical. It should be noted that the angle shown in FIG. 2 is exaggerated for purposes of illustration. It should be noted that the cruciform pendulum is balanced so that the center of mass coincides with a cross-point of an axis O-O' and an axis A of rigid rod 16 when the cruciform pendulum is vertical; i.e., when the angle $\phi$ is zero. This prevents sliding of the cruciform pendulum with respect to samples 12 in the presence of vibrations or other external forces.

The value of angle $\phi$ varies over time, thus we may consider a time-dependent angular displacement $\phi(t)$. As will be seen in the calculations below, it is useful to define a time-dependent amplitude of oscillation $\alpha(t)$, such that $$\phi(t) = \alpha(t)\cos\frac{2\pi}{T}t,$$

where T is the mean period of oscillation. In order to measure $\phi(t)$, a fixed laser 30 generates a beam 36, which is reflected from a planar reflector 34 mounted on the rigid rod 16. As shown, the planar reflector 34 extends vertically along the axis A of rigid rod 16, and extends horizontally in the direction of horizontal support 26. The axis of rotation O-O' of the pendulum bisects the reflector 34. As the rigid rod 16 rotates through angle $\phi$ with respect to the horizontal, the planar reflector 34 also rotates by angle $\phi$ with respect to the horizontal, and the angular deflection of the beam 36 is picked up and measured by a photodetector 32. It should be understood that any suitable light source may be utilized for generating the light beam 36, and that any suitable type of photodetector 32, such as a charge-coupled device, may be used for measuring the angular deflection $\phi$. The laser 30 may also be used in combination with any suitable optics for focusing or the like, as is conventionally known. It should be noted that the actual angle of reflection between the source 30 and the detector 32 is $2\phi$. Thus, the actual measured angle is simply halved to produce $\phi$.

With the accurate measurement of angular deflection $\phi$ by the photodetector 32, a mean value of a dimensionless coefficient of rolling friction between the hemispherical sample 12 and the flat surface sample 14 may be calculated as $$f = \frac{\cos\alpha_n - \cos\alpha_0}{2(\alpha_0 + \alpha_n) + 4\sum_{i=1}^{n-1}\alpha_i},$$

where $\alpha_0$ is an initial angular amplitude of pendulum oscillation, $\alpha_n$ is a final angular amplitude of pendulum oscillation, and $\alpha_i$ is an angular amplitude in an intermediate cycle of pendulum oscillation i. For each small oscillation of the pendulum, the angular deflection $\phi$ is measured for each full cycle, ranging from $\phi(t_0)$ to $\phi(t_n)$, where $t_0$ is the time of initial measurement (i.e., the greatest value of $\phi$) and $t_n$ being the time of final measurement, such that an instantaneous time $t_i$ is defined with i=0, 1, 2, 3, ..., n. The period of each full cycle $T_i$ is measured by a timer 40. Thus, $\alpha_i$ is calculated as $$\phi(t_i)\sec\left(\frac{2\pi}{T}t_i\right),$$

$\alpha_0$ is calculated as $$\phi(t_0)\sec\left(\frac{2\pi}{T}t_0\right)$$

and $\alpha_n$ is calculated as $$\phi(t_n)\sec\left(\frac{2\pi}{T}t_n\right),$$

where T is the measurement average of all of the $T_i$.

The dependence of $\alpha$ with respect to time can be approximated using the analytic function of regression, where b and p are the parameters of regression, as $$\alpha(t) = \alpha_0\left(1 - 4\frac{b}{\alpha_0^{1-p}}\frac{1-p}{1+p}\cdot\frac{t}{T}\right)^{\frac{1}{1-p}}.$$

Further, the moment of rolling friction, as a function of the angular deflection $\phi$, $M_{fr}(\phi)$ between hemispherical sample 12 and planar surface sample 14 can be calculated as $$M_{fr}(\phi) = -mgRb\phi^p \cdot \text{sign}\left(\frac{d\phi}{dt}\right),$$

where in represents the overall mass of the pendulum apparatus, g is the gravitational acceleration, and R is the radius of the hemispherical sample 12. The function "sign" is determined by the direction of oscillation; i.e., by the sign of $$\frac{d\phi}{dt}.$$

Further, the hysteresis losses $W(\alpha_i)$ for each cycle of the pendulum oscillation with amplitude $\alpha_i$ may be calculated as $$W(\alpha_i) = 4mgRb\frac{\alpha_i^{1+p}}{1+p}.$$

Above, the mean value of the dimensionless coefficient of rolling friction f between hemispherical sample 12 and flat surface sample 14 was calculated as a function of $\alpha_0$ and $\alpha_n$. The instantaneous value $f_\phi$ may be calculated as $$f_\phi = \frac{|M_{fr}(\phi)|}{mgR} = b\phi^p.$$

Additionally, the approximation of the dependence $T_i$ on $\alpha_i$ with the analytic function of regression may be calculated as:

$$T(\alpha) = T_0\left[1 - \sqrt{\pi}\,\gamma\frac{a^2\alpha^q}{gm}\frac{\Gamma\left(\frac{q}{2}+\frac{3}{2}\right)}{\Gamma\left(\frac{q}{2}+2\right)}\cdot\left(1 - 0.55\frac{R\alpha}{a}\right)\right]^{-1},$$

where a is the radius of the contact spot between the sample 12 and the sample 14, $T_0$, $\gamma$ and q are the parameters of regression (determined by experiment of cycling time intervals versus rolling body displacement), and $\Gamma$ is the gamma function. The parameter $\gamma$ is a pressure of an adhesion force between hemispherical samples 12 and the flat surface samples at points of contact therebetween.

Additionally, the moment of elastic rolling resistance $M_{el}(\phi)$ may be calculated as $$M_{el}(\phi) = 2\gamma a^2 R|\phi|^{q+1}\left(\frac{\pi}{2} - \frac{R}{a}\phi\right)\cdot\text{sign}(\phi).$$

The full moment of rolling resistance is then, simply, $M(\phi) = M_{fr}(\phi) + M_{el}(\phi)$. As noted above, since pre-rolling is the stage of consideration, the angular displacement is preferably within the limit of $$\phi \leq 0.1\frac{a}{R}.$$

As shown in FIG. 1, the system 10 is symmetric about the vertical axis. A pair of holders 24 is provided for retaining the pair of hemispherical samples 12, which contact identical flat surface samples 14. This arrangement prevents any friction-based torque from being introduced into the experiment (i.e., unwanted rotation about the vertical axis). Further, as shown in FIG. 1, upper and lower adjustable weights 42, 44 may be provided on the rod 16 for large-scale adjustment of the oscillation of rod 16, and additional smaller weights 46 may be provided for fine-scale adjustment. As shown, the smaller weights 46 are preferably adjustably mounted on a rod 48 that extends orthogonal to the axis of rod 16 and also to the axis of rotation O-O' of the pendulum.

It is to be understood that the present invention is not limited to the embodiments described above, but encompasses any and all embodiments within the scope of the following claims.

We claim:

1. A system for measuring rolling resistance, comprising:

an elongated rigid rod having opposed upper and lower ends, the upper and lower ends being free;

an elongated horizontal support rigidly mounted on a central portion of the rigid rod, the horizontal support extending orthogonal to the rigid rod;

a pair of retainers extending downward from opposing ends of the horizontal support, respectively, each of the retainers having a free end adapted for rigidly holding a sample of a first test material so that a hemispherical portion of the first material protrudes from the free end of each of the retainers, the rod, the horizontal support, and the retainers forming a substantially cruciform pendulum adapted for being supported by the hemispherical portion of the first test material bearing upon a flat planar sample of a second test material, the first test material rolling upon the second test material when the rigid rod is deflected and released to produce an oscillating pendulum motion;

a planar reflector mounted on the central portion of the rigid rod;

a light source for generating a coherent light beam focused on the reflector;

a photodetector positioned to receive a reflection of the coherent light beam when the light beam is reflected off of the planar reflector in order to determine an angular deviation $\phi$ measuring deflection of the rigid rod with respect to vertical; and a timer in communication with the photodetector for measuring a time-dependency of angular deviation $\phi$ and for timing periods of oscillation of the cruciform pendulum.

2. The system for measuring rolling resistance according to claim 1, further comprising a pair of horizontally disposed, spaced apart support surfaces adapted for supporting the flat planar sample of the second test material, the support surfaces being spaced apart so that the ends of the horizontal support and the retainers holding the hemispherical portions of the samples of the first test material are disposed above the support surfaces and the rigid rod is free to oscillate in a plane between the support surfaces, wherein a center of mass of the cruciform pendulum is located centrally between upper ends of the hemispherical portions.

3. The system for measuring rolling resistance according to claim 1, wherein the timer is configured for measuring a time $t_i$ and a period of oscillation $T_i$ for each cycle of oscillation of the cruciform pendulum, each period $T_i$ corresponding to the time $t_i$, where i is an integer ranging between zero and n, where n represents a final measurement, an initial amplitude of oscillation $\alpha_0$ being defined as $$\alpha_0 = \phi(t_0)\sec\left(\frac{2\pi}{T}t_0\right),$$

a final amplitude of oscillation $\alpha_n$ being defined as $$\alpha_n = \phi(t_n)\sec\left(\frac{2\pi}{T}t_n\right)$$

and an intermediate amplitude of oscillation $\alpha_i$ being defined as $$\alpha_i = \phi(t_i)\sec\left(\frac{2\pi}{T}t_i\right),$$

where T is a mean value of the $T_i$, a dimensionless coefficient of rolling friction f between the pair of hemispherical samples and the flat surface samples being calculated as $$f = \frac{\cos\alpha_n - \cos\alpha_0}{2(\alpha_0 + \alpha_n) + 4\sum_{i=1}^{n-1}\alpha_i}.$$

4. The system for measuring rolling resistance as recited in claim 1, further comprising means for selectively adjusting the oscillation of the cruciform pendulum.

5. The system for measuring rolling resistance as recited in claim 4, wherein the means for selectively adjusting the oscillation of the cruciform pendulum comprises a first mass adjustably mounted to said rigid rod.

6. The system for measuring rolling resistance as recited in claim 5, wherein the means for selectively adjusting the oscillation of the cruciform pendulum further comprises a second mass adjustably mounted to said rigid rod beneath the horizontal support, the first mass being mounted to said rigid rod above the horizontal support, the first and second masses being adjustably positioned along said rigid rod.

7. The system for measuring rolling resistance as recited in claim 4, wherein the means for selectively adjusting the oscillation of the cruciform pendulum further comprises:
an auxiliary rod secured to said rigid rod adjacent the horizontal support, the auxiliary rod extending perpendicular to a plane defined by said rigid rod and said horizontal support; and
a pair of fine-adjustment masses adjustably mounted to the auxiliary rod, adjacent opposed ends thereof.

8. A method for measuring rolling resistance, comprising the steps of:
providing a cruciform pendulum, the cruciform pendulum including an elongated rigid rod having opposed upper and lower ends, the upper and lower ends being free to rotate, and an elongated horizontal support mounted on a central portion of the rigid rod, the horizontal support extending orthogonal to the rigid rod, the horizontal support having sample holders extending downward from opposing ends of the horizontal support, the rigid rod having a reflector mounted thereon between the sample holders;
rigidly mounting samples of a first test material in the sample holders so that a hemispherical portion of the first test material protrudes from the sample holders;
to placing flat planar samples of a second test material on spaced apart horizontal supports;
suspending the cruciform pendulum between the spaced apart horizontal supports with the hemispherical portion of the first test material resting on the flat planar samples of the second test material;
deflecting the rigid rod by a small initial angular deviation $\phi$ from vertical;
releasing the rigid rod to induce pendulum oscillations, the hemispherical portion of the first test material rolling forward and backward on the second test material;
optically measuring the angular deviation $\phi$ of the of the rigid rod with respect to the vertical;
measuring the period $T_i$ of oscillation for each cycle of oscillation of the cruciform pendulum, each period $T_i$ corresponding to a time $t_i$, wherein i is an integer ranging between zero and n, wherein n represents a final measurement;
calculating an initial amplitude of oscillation $\alpha_0$ as $$\alpha_0 = \phi(t_0)\sec\left(\frac{2\pi}{T}t_0\right),$$

an intermediate amplitude of oscillation $\alpha_i$ as $$\alpha_i = \phi(t_i)\sec\left(\frac{2\pi}{T}t_i\right),$$

and a final amplitude of oscillation $\alpha_n$ as $$\alpha_n = \phi(t_n)\sec\left(\frac{2\pi}{T}t_n\right),$$

wherein T is a mean value of the $T_i$; and
calculating a dimensionless coefficient of rolling friction f between the pair of hemispherical samples and stationary flat planar samples formed from the second material as $$f = \frac{\cos\alpha_n - \cos\alpha_0}{2(\alpha_0 + \alpha_n) + 4\sum_{i=1}^{n-1}\alpha_i}.$$

9. The method for measuring rolling resistance as recited in claim 8, further comprising the step of calculating a pair of parameters of regression b and p as $$\alpha(t) = \alpha_0 \left(1 - 4\frac{b}{\alpha_0^{1-p}} \frac{1-p}{1+p} \cdot \frac{t}{T}\right)^{\frac{1}{1-p}}.$$

10. The method for measuring rolling resistance as recited in claim 7, further comprising the step of calculating a moment of rolling friction $M_{fr}(\phi)$ as $M_{fr}(\phi) = \pm mgRb\phi^p$, wherein in represents an overall mass of the cruciform pendulum, g is the gravitational acceleration, and R is a radius of each hemispherical sample.

11. The method for measuring rolling resistance as recited in claim 10, further comprising the step of calculating hysteresis losses $W(\alpha_i)$ for each cycle of the cruciform pendulum oscillation as $$W(\alpha_i) = 4mgRb\frac{\alpha_i^{1+p}}{1+p}.$$

12. The method for measuring rolling resistance as recited in claim 11, further comprising the step of calculating an instantaneous dimensionless coefficient of rolling friction $$f_\phi \text{ as } f_\phi = \frac{|M_{fr}(\phi)|}{mgR} = b\phi^b.$$

13. The method for measuring rolling resistance as recited in claim 12, further comprising the step of calculating a moment of elastic rolling resistance $M_{el}(\phi)$ as $$M_{el}(\phi) = \pm 2\gamma a^2 R |\phi|^{n+1}\left(\frac{\pi}{2} - \frac{R}{a}\phi\right),$$

where q is a parameter of regression from an analytic function of regression given by:

$$T(\alpha) = T_0 \left[1 - \sqrt{\pi}\, \gamma \frac{a^2 \alpha^q}{gm} \frac{\Gamma\left(\frac{q}{2} + \frac{3}{2}\right)}{\Gamma\left(\frac{q}{2} + 2\right)} \cdot \left(1 - 0.55\frac{R\alpha}{a}\right)\right]^{-1},$$

wherein a is a radius of a contact spot between each said hemispherical sample and the corresponding one of the flat planar samples, and γ is a pressure of adhesion between the hemispherical samples and the corresponding flat planar samples.

14. The method for measuring rolling resistance as recited in claim 8, wherein the cruciform pendulum has an angular deviation φ in the range $$\phi \leq 0.1\frac{a}{R},$$

wherein a is a radius of a contact spot between each said hemispherical sample and the corresponding one of the flat surface samples and R is a radius of each said hemispherical sample.

15. The method for measuring rolling resistance as recited in claim 8, further comprising the steps of:
    providing an auxiliary rod attached to the rigid rod, the auxiliary rod extending orthogonal to a plane defined by the rigid rod and the horizontal support; and
    adjustably mounting at least one weight on the auxiliary rod to shift the cruciform pendulum's center of mass forward and rearward of vertical.

16. The method for measuring rolling resistance as recited in claim 8, wherein said step of optically measuring the angular deviation φ of the of the rigid rod comprises the steps of:
    aiming an incident beam of coherent light from a laser at a reflector mounted on the rigid rod;
    detecting a reflected beam of the coherent light with a photodetector;
    calculating the angle between the incident light beam and the reflected beam; and
    dividing the angle between the incident light beam and the reflected beam by two in order to obtain φ.

* * * * *